United States Patent [19]
Schone

[11] Patent Number: 5,998,696
[45] Date of Patent: Dec. 7, 1999

[54] SANITARY ARTICLES WITH MULTI APERTURE SIZE FILM TOPSHEETS

[75] Inventor: Rainer Walter Max Schone, Konigstein, Germany

[73] Assignee: The Procter & Gamble Company, Cincinnati, Ohio

[21] Appl. No.: 09/029,437

[22] PCT Filed: Aug. 30, 1996

[86] PCT No.: PCT/US96/13989

§ 371 Date: Oct. 2, 1998

§ 102(e) Date: Oct. 2, 1998

[87] PCT Pub. No.: WO97/09020

PCT Pub. Date: Mar. 13, 1997

[30] Foreign Application Priority Data

Sep. 6, 1995 [EP] European Pat. Off. .............. 95113943

[51] Int. Cl.[6] ............................. A61F 13/15; A61F 13/20
[52] U.S. Cl. ........................ 604/378; 604/368; 604/385.1
[58] Field of Search ..................................... 604/378, 368, 604/385.1, 387

[56] References Cited

U.S. PATENT DOCUMENTS

| | | |
|---|---|---|
| 4,217,901 | 8/1980 | Bradstreet et al. . |
| 4,342,314 | 8/1982 | Radel et al. . |
| 4,463,045 | 7/1984 | Ahr et al. . |
| 4,508,256 | 4/1985 | Radel et al. . |
| 4,609,518 | 9/1986 | Curro et al. . |
| 4,637,819 | 1/1987 | Ouellette et al. . |
| 4,798,603 | 1/1989 | Meyer et al. . |
| 5,342,334 | 8/1994 | Thompson et al. . |
| 5,399,411 | 3/1995 | Suzuki et al. . |
| 5,415,640 | 5/1995 | Kirby et al. . |
| 5,500,270 | 3/1996 | Langdon et al. . |
| 5,514,105 | 5/1996 | Goodman, Jr. et al. . |
| 5,522,811 | 6/1996 | Igaue et al. . |
| 5,533,991 | 7/1996 | Kirby et al. ............................ 604/378 |
| 5,669,899 | 9/1997 | Osborn, III . |

*Primary Examiner*—Mark O. Polutta
*Attorney, Agent, or Firm*—Matthew P. Fitzpatrick; Jeffrey V. Bamber; Jacobus C. Rasser

[57] ABSTRACT

The present invention relates to absorbent articles particularly sanitary napkins having film topsheets. In particular a film topsheet receiving the liquids to be absorbed comprises apertures of at least 4 different sizes. This range of aperture sizes provides exceptionally good liquid intake performance for the range of liquid viscosities commonly found for liquids which are absorbed in sanitary napkins.

8 Claims, 2 Drawing Sheets

SANITARY ARTICLES WITH MULTI APERTURE SIZE FILM TOPSHEETS

FIELD OF THE INVENTION

The present invention relates to absorbent articles particularly sanitary napkins having film topsheets. In particular a film topsheet receiving the liquids to be absorbed comprises apertures of at least 4 different sizes. This range of aperture sizes provides exceptionally good liquid intake performance for the range of liquid viscosities commonly found for liquids which are absorbed in sanitary napkins.

BACKGROUND OF THE INVENTION

Sanitary articles such as sanitary napkins, baby diapers, absorbent inserts, and absorbent adult incontinence articles are well-known in the art. Typically all these articles comprise a wearer facing surface and a garment facing surface. The wearer facing surface receives from the wearer of such articles liquids, bodily discharges such as urins, vaginal discharges or menses, to be absorbed. In order for the article to store the liquid the wearer facing surface has to be liquid permeable while maintaining integrity of the outer wearer facing surface of the absorbent article. This wearer facing surface is provided by a topsheet.

Well-known topsheets in the art of absorbent articles are non-woven fabrics, woven fabrics or films. Films have to be rendered permeable by aperturing. Fabrics or non-woven fabrics are made of fibers which by their nature provide non-linear apertures in the liquid transport direction. Also the largest aperture size in fabric topsheets is limited by the requirement to maintain material strength.

Films are often made of polymeric material and typically comprise apertures which have been engineered to provide certain characteristics. These apertures can vary in shape and size but have commonly been provided in a single preferred size and shape. The walls of the apertures define the amount of extension-if any- beyond the plane of the film thickness and the direction of such extensions. The film apertures also can be provided in the shape of a funnel. Films are generally preferred over fabrics since they can provide a cleaner surface even after liquid having passed through since they do not retain liquids.

A typical topsheet made of polyethylene film has been successfully used in sanitary articles and adult incontinence products as well as inserts and baby diapers. One problem remaining is the rate of liquid capable of passing through such a topsheet under usual usage conditions due to the total amount of open area of all apertures and individual aperture size and shape in particular. Exceptionally large apertures increase the liquid passage rate but pose the potential problem of material stability for the topsheet film at least during the manufacturing of absorbent articles, which is highly undesirable. Also large apertures possibly promote a backflow of absorbed liquid, so called rewet, which is undesirable. Small individual apertures on the other hand cannot provide the liquid passage characteristics required to let liquids of high surface tension, high viscosity or solid content such as coagulated blood clots pass through; this can be a problem in an absolute sense for very small apertures or cause too low a rate of liquid flow.

It also has been found that the total amount of open area for a given aperture size and shape is approximately linearly related to the rate of liquid passage. Again, masking of the liquid which has passed through but also material strength and other appearance considerations are limiting the extend as to which the total open area in a film topsheet can be selected.

It is also known that the viscosity of liquids disposed on sanitary napkins can vary drastically from exceptionally low viscosities e.g. of urine from a person having a light incontinence or stress incontinence syndrome. Low viscosities also can be present for vaginal discharges or menses which comprise small amounts of surfactant. Some bodily discharges comprise natural surfactants already but also residue from washing soaps, which many wearers of such articles use regularly, can be found.

At the other end of the spectrum viscosities of menses changes drastically over the period of a woman and have been reported in EP-A-0 205 286 to range from 5 to 50 mPas. The viscosities can change over time on the same person and can vary between persons compared at a similar stage of the monthly period.

It is therefore an objective of the present invention to provide a film topsheet for sanitary articles which can accommodate the viscosity changes without the need for different articles for different times. It has been found that this can be achieved by providing topsheets for absorbent disposable articles which have apertures of different open areas. These open areas should correspond to a range of the viscosity distribution of the liquids expected to be absorbed.

It is hence an objective of the present invention to provide absorbent articles which have a film topsheet with a distribution of aperture sizes.

DESCRIPTION OF THE INVENTION

Figure 1:
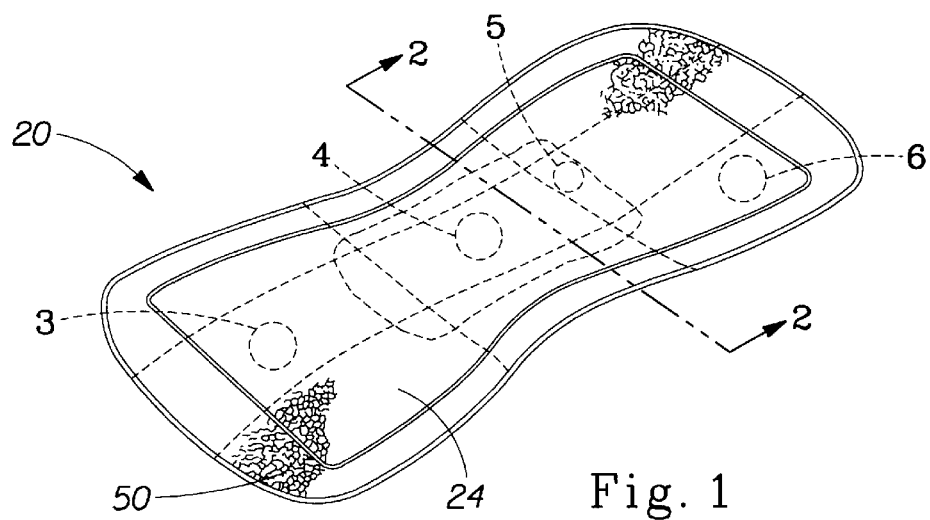
FIG. 1 is a top plan view of an absorbent article having a topsheet of the present invention. A portion of the apertured structure is shown on the surface of the topsheet.
Figure 2:
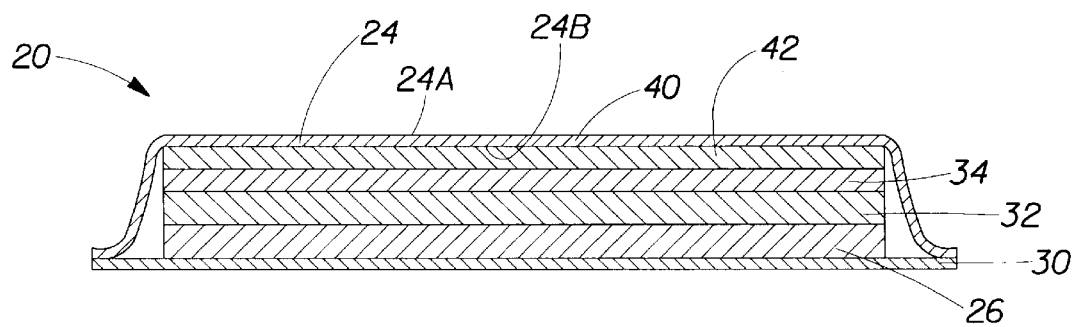
FIG. 2 is a cross section view of the absorbent article shown in FIG. 1, taken along line 2—2.
Figure 3:
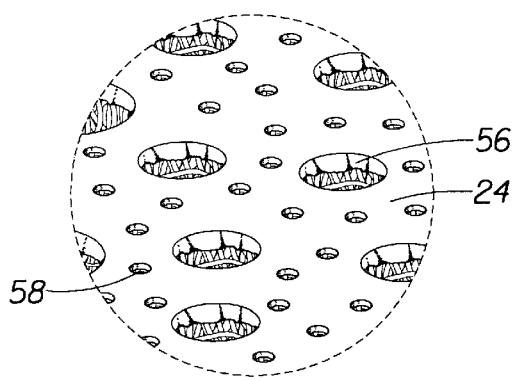
FIG. 3 is an enlarged top plan view of area "A" from FIG. 1 showing the details of the apertures in the indicated region of the absorbent article.
Figure 4:
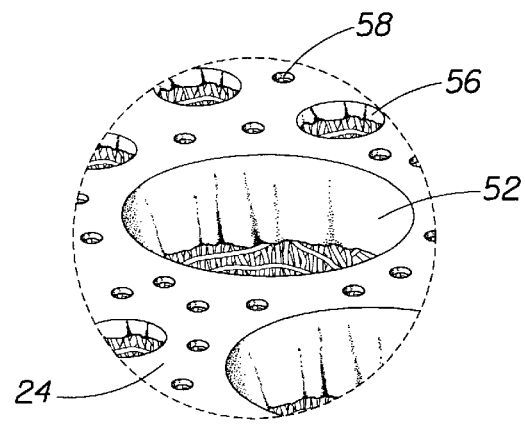
FIG. 4 is an enlarged top plan view of area "B" from FIG. 1 showing the details of the apertures in the indicated region of the absorbent article.
Figure 5:
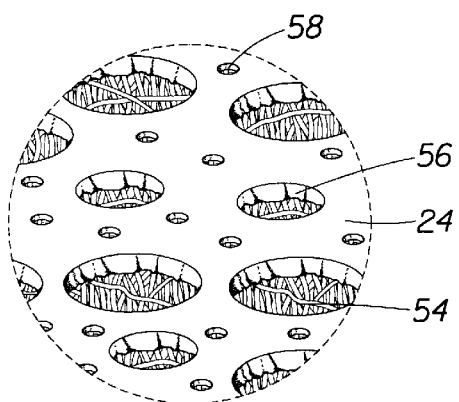
FIG. 5 is an enlarged top plan view of area "C" from FIG. 1 showing the details of the apertures in the indicated region of the absorbent article.
Figure 6:
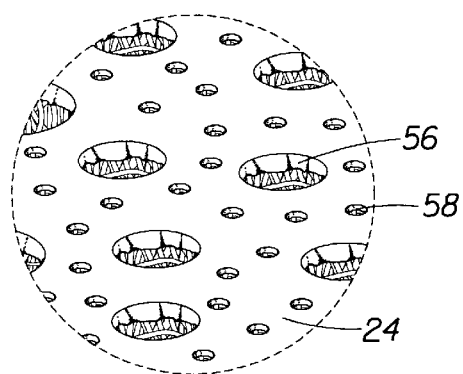
FIG. 6 is an enlarged top plan view of area "D" from FIG. 1 showing the details of the apertures in the indicated region of the absorbent article.

The present invention provides an absorbent article such as absorbent article 20 shown in FIGS. 1–6 having the benefit of an aperture film topsheet for liquids of drastically different viscosities. In particular, the absorbent article comprises a topsheet 24 having a wearer facing surface 24A and a garment facing surface 24B. The topsheet 24 can comprise multiple layers which are preferably joined to each other. An absorbent article generally further comprises a backsheet 30 and an absorbent structure, alternatively called absorbent core, placed between the topsheet 24 and the backsheet 26.

Absorbent Structure

The absorbent structure can include the following components: (a) optionally a primary fluid distribution layer 42 preferably together with a secondary optional fluid distribution layer 34; (b) a fluid storage layer 32; (c) optionally a fibrous ("dusting") layer 26 underlying the storage layer; and (d) other optional components.

a Primary/Secondary Fluid Distribution Layer

One optional component of the absorbent structure according to the present invention is a primary fluid distribution layer 42 and a secondary fluid distribution layer 34. The primary distribution layer 42 typically underlies the topsheet 24 and is in fluid communication therewith. The topsheet transfers the acquired fluid to this primary distribution layer for ultimate distribution to the storage layer 32. This transfer of fluid through the primary distribution layer 42 occurs not only in the thickness, but also along the length and width directions of the absorbent product. The also optional but preferred secondary distribution layer 34 typically underlies the primary distribution layer 42 and is in fluid communication therewith. The purpose of this secondary distribution layer 34 is to readily acquire fluid from the primary distribution layer 42 and transfer it rapidly to the underlying storage layer 32. This helps the fluid capacity of the underlying storage layer to be fully utilised. The fluid distribution layers can be comprised of any material typical for such distribution layers. In particular fibrous layers maintain the capillaries between fibers even when wet are useful as distribution layers.

b Fluid Storage Layer

Positioned in fluid communication with, and typically underlying the primary or secondary distribution layers, is a fluid storage layer 32. The fluid storage layer 32 can comprise any usual absorbent material or combinations thereof. It preferably comprises absorbent gelling materials usually referred to as "hydrogel", "superabsorbent", "hydrocolloid" materials in combination with suitable carriers.

The absorbent gelling materials are capable of absorbing large quantities of aqueous body fluids, and are further capable of retaining such absorbed fluids under moderate pressures. The absorbent gelling materials can be dispersed homogeneously or non-homogeneously in a suitable carrier. The suitable carriers, provided they are absorbent as such, can also be used alone.

Suitable absorbent gelling materials for use herein will most often comprise a substantially water-insoluble, slightly cross-linked, partially neutralised, polymeric gelling material. This material forms a hydrogel upon contact with water Such polymer materials can be prepared form polymerizable, unsaturated, acid-containing monomers which are well known in the art.

Suitable carriers include materials which are conventionally utilised in absorbent structures such as natural, modified or synthetic fibers, particularly modified or non-modified cellulose fibers, in the form of fluff and/or tissues. Suitable carriers can be used together with the absorbent gelling material, however, they can also be used alone or in combinations. Most preferred are tissue or tissue laminates in the context of sanitary napkins/panty liners.

An embodiment of the absorbent structure made according to the present invention comprises a double layer tissue laminate formed by folding the tissue onto itself. These layers can be joined to each other for example by adhesive or by mechanical interlocking or by hydrogen bridge bands. Absorbent gelling material or other optional material can be comprised between the layers.

Modified cellulose fibers such as the stiffened cellulose fibers can also be used. Synthetic fibers can also be used and include those made of cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like. Preferably, the fiber surfaces are hydrophilic or are treated to be hydrophilic. The storage layer can also include filler materials, such as Perlite, diatomaceous earth, Vermiculite, etc., to improve liquid retention.

If the absorbent gelling material is dispersed non-homogeneously in a carrier, the storage layer can nevertheless be locally homogenous, i.e. have a distribution gradient in one or several directions within the dimensions of the storage layer. Non-homogeneous distribution can also refer to laminates of carriers enclosing absorbent gelling materials partially or fully.

c Optional Fibrous ("Dusting") Layer

An optional component for inclusion in the absorbent structure according to the present invention is a fibrous layer 26 adjacent to, and typically underlying the storage layer 32. This underlying fibrous layer 26 is typically referred to as a "dusting" layer since it provides a substrate on which to deposit absorbent gelling material in the storage layer during manufacture of the absorbent structure. Indeed, in those instances where the absorbent gelling material is in the form of macro structures such as fibers, sheets or strips, this fibrous "dusting" layer need not be included. However, this "dusting" layer provides some additional fluid-handling capabilities such as rapid wicking of fluid along the length of the pad.

d Other Optional Components of the absorbent structure

The absorbent structure according to the present invention can include other optional components normally present in absorbent webs. For example, a reinforcing scrim can be positioned within the respective layers, or between the respective layers, of the absorbent structure. Such reinforcing scrims should be of such configuration as to not form interfacial barriers to fluid transfer. Given the structural integrity that usually occurs as a result of thermal bonding, reinforcing scrims are usually not required for thermally bonded absorbent structures.

Another component which can be included in the absorbent structure according to the invention and preferably is provided close to or as part off the primary or secondary fluid distribution layer are odor control agents. Active carbon coated with or in addition to other odor control agents, in particular suitable zeolite or clay materials, are optionally incorporated in the absorbent structure. These components can be incorporated in any desired form but often are included as discrete particles.

Backsheet

The backsheet 30 primarily prevents the exudates absorbed and contained in the absorbent structure from wetting articles that contact the absorbent product such as underpants, pants, pyjamas and undergarments. The backsheet 30 is preferably impervious to liquids (e.g. menses and/or urine) and is preferably manufactured from a thin plastic film, although other flexible liquid impervious materials can also be used. As used herein, the term "flexible" refers to materials that are compliant and will readily conform to the general shape and contours of the human body. The backsheet also can have elastic characteristics allowing it to stretch in one or two directions.

The backsheet 30 typically extends across the whole of the absorbent structure and can extend into and form part of or all of the preferred sideflaps, side wrapping elements or wings.

The backsheet 30 can comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils).

Exemplary polyethylene films are manufactured by Clopay Corporation of Cincinnati, Ohio, under the designation P18-0401 and by Ethyl Corporation, Visqueen Division, of Terre Haute, Ind., under the designation XP-39385.The backsheet is preferably embossed and/or matte finished to provide a more clothlike appearance. Further,. the backsheet can permit vapours to escape from the absorbent structure, i.e. be breathable, while still preventing exudates from passing through the backsheet. Also breathable backsheets comprising several layers, e.g. film plus non-woven structures, can be used.

The Topsheet

For multiple layer topsheets the term "joined", as used herein, encompasses configurations in which the first layer is directly secured to the second layer by affixing the first layer directly to the second layer; configurations in which the first layer is indirectly secured to the second layer by affixing the first layer to intermediate layer(s) which in turn are affixed to the second layer:

The layers of the topsheet 24 can preferably be joined together by adhesives, stitching, heat and/or pressure bonds, dynamic mechanical bonds, ultrasonic bonds, intermingling or entanglement of structural elements comprising the layers of the topsheet, such as by extruding one layer onto another, or by any other means known in the art.

The topsheet as a whole and hence each layer individually needs to be compliant, soft feeling, and non-irritating to the wearer's skin. It also can have elastic characteristics allowing it to be stretched in one or two directions.

According to the present invention at least one layer of the topsheet 24 is provided by a film material having apertures 50 which are referred herein as "extra large apertures 52", "large apertures 54", "medium apertures 56" and "small apertures" 58. These apertures are provided to facilitate liquid transport for liquids of various viscosities from the wearer facing surface towards the absorbent structure.

For all measurements regarding the apertures in the film passage layer the plane of the smallest cross sectional areas of the aperture should be used, unless otherwise mentioned. The term "aperture size" as used herein refers to the open area which an aperture provides in the film.

The "extra large apertures" 52 have an individual open area of from more than 1.4 $mm^2$, to 3 $mm^2$. The total open area of the "extra large apertures" 52 excluding all other liquid transport apertures should be in the range from 1% to 25%, preferably from 10% to 20% of the surface area of the topsheet 24.

The "large apertures" 54 have an individual open area of from more than 0.5 $mm^2$, to 1.4 $mm^2$. The total open area of the "large apertures" 54 excluding all other liquid transport apertures should be in the range from 1% to 30%, preferably from 5% to 15% of the surface area of the topsheet 24.

The "medium apertures" 56 have an individual open area of from more than 0.1 $mm^2$, to 0.5 $mm^2$. The total open area of the "medium apertures" 56 excluding all other liquid transport apertures should be in the range from 1% to 35%, preferably from 10% to 25% of the surface area of the topsheet 24. The "small apertures" 58 have an individual open area of from more than 0 $mm^2$, to 0.1 $mm^2$. The total open area of the "small apertures" 58 excluding all other liquid transport apertures should be in the range from 0.1% to 5%, preferably from 0.5% to 3% of the surface area of the topsheet 24.

The apertures 50 are preferably substantially circular or polygonal. Their shape is limited by having a ratio of the largest to the smallest inner diagonal length in the range between 1 and 6,preferably 1 and 3. The total open area of all liquid transport apertures is in the range of 3.1% to 95%, preferably 10% to 50%,most preferably 15% to 40% of the total area of the topsheet. Topsheets 29 can have a homogeneous or non-homogeneous distribution of liquid passage ways. The later would have a highest concentration of apertures in the area where liquid is expected to be discharged to.

The liquid transport apertures can be simple holes but preferably are formed in the film such that the walls of the apertures extend beyond the plane of the surface of the basic film, i.e. the film surface, before the film is apertured. The direction of these extending walls in the absorbent article is towards the garment facing surface of the article. The amount of extension of the walls of the apertures should be at least 0.3 mm beyond the film surface from which the walls of the apertures depend. Preferably the walls of the apertures form funnels or Ventury channels as is well-known in the art.

To ensure material stability the smallest distance between neighbouring extra large and/or large apertures regardless of their particular shape and size is preferably at least 0.5 mm, preferably 1.5 mm. This distance is measured on the surface of the film on the side closest to the user facing surface of the absorbent article.

The film material is preferably rendered hydrophilic to such a degree that the contact angle is less than 90° with distilled water upon first contact with the water. For films this can be achieved by surfactant treatment. For surfactant treated polymeric films it has been found that it is beneficial to use films where the surfactant is permanently fixed on the film surface. These are so called film materials with resin integrated surfactant. For these films even repeated wetting by distilled water would provide approximately the same contact angle as the first contact with distilled water.

In another preferred execution the wearer facing surface of the topsheet 24 is treated with an agent such that liquids are directed towards the apertures 50. Such agents can be silicone or teflon which provide the treated surface with a self-cleaning effect. This treatment can be in addition to the above-mentioned surfactant treatment.

Films such as those disclosed in EP-0 205 286, EP-0 165 208, EP-0 18 020, EP-0 59 506 or U.S. Pat. No. 3,929,135 are explicitly referred to as suitable for the topsheet provided the requirements for the aperture distribution is met. Other suitable formed films, also provided the requirements for the aperture distribution are met, are described in EP-203 820, U.S. Pat. No. 4,324,246, U.S. Pat. No. 4,342,314, U.S. Pat. No. 4,463,045 and U.S. Pat. No. 5,006,394. Particularly preferred microaperturing of formed film is disclosed in U.S. Pat. No. 4,609,518 and U.S. Pat. No. 4,629,643. These microapertures can also be included in the topsheet provided their surface is less than 0.15 $mm^2$ and hence they essentially provide breathability. Ways of making such films are well-known in the art and have also been disclosed in the above prior art references. Also films which are, prior to aperturing, water vapour permeable but liquid impermeable can be used in the context of the present invention.

If the topsheet 24 comprises multiple layers the second and following layers can be of the same kind as the above described topsheet according to the present invention with an aperture distribution. They can also be provided by other film layers or by woven or non-woven layers.

It is recommendable that any additional layer presents no barrier for the liquid. This can be achieved by providing no hydrophilicity gradient or an absorbency driving hydrophilicity gradient such that a directing force for the liquid towards the absorbent structure is created. It is also considered desirable that all layers have about the same total open area.

While not wishing to be limited by theory it is believed that a constant Reynolds number could ensure optimum liquid passage rates. The optimum Reynolds number depends of course on the absorption speed of the absorbent core. Once this Reynolds number is established for a particular liquid viscosity, absorbent core and one apertures size, the theoretically ideal distribution of aperture sizes can be identified by the equation.

$$\text{Reynolds number} = \frac{\text{density} \cdot \text{flow speed} \cdot \text{hydraulic diameter}}{\text{viscosity}}$$

wherein
  density is the density of the liquid to be absorbed in units of mass over volume,
  flow speed is the velocity of the liquid to be absorbed in units of distance over time,
  hydraulic diameter can be calculated from the size of the aperture as the square route of 4 times the aperture size over Pi.
  viscosity is the dynamic viscosity of the liquid to be absorbed in units of pressure times time.

With density being approximately constant (about that of water) and flow speed being constant by desire the hydraulic diameter distribution becomes approximately linearly proportional to the viscosity and the aperture size distribution becomes approximately proportional to the square of the viscosity:

$$\text{aperture size} \sim \text{viscosity}^2$$

Following this theory it is easy to select for a viscosity profile, which is expected over the usage conditions for a certain topsheet the aperture size distribution which is theoretically ideal. From this theoretically ideal distribution a realistic approximation with at least 4 different aperture sizes can be selected to provide a topsheet according to the present invention.

Preferred film topsheet according to the present invention have a larger number than 4 apertures, preferably the "theoretically ideal distribution of apertures" is resembled by a distribution of 5, 6, 7, 8, 9 or even 10 different aperture sizes. The majority of benefits from an aperture distribution are however already realized by 5, 6, 7 or 8 different aperture sizes. The distribution must still satisfy the distribution given for 4 apertures, preferably with a skew towards the center of the distribution.

What is claimed is:

1. An absorbent article comprising a topsheet, a backsheet, and an absorbent structure placed between said topsheet and said backsheet, said topsheet having a wearer facing surface and a garment facing surface and said topsheet comprising a film passage layer having small, medium, large and extra-large apertures for liquid transport,
  said small apertures have an individual area in the range from more than 0 mm$^2$ to 0.1 mm$^2$,
  said medium apertures have an individual area in the range from more than 0.1 mm$^2$ to 0.5 mm$^2$,
  said large apertures have an individual area in the range from more than 0.5 mm$^2$ to 1.4 mm$^2$,
  said extra-large apertures have an individual area in the range from more than 1.4 mm$^2$ to 3 mm$^2$,
  said small apertures have a total open area in the range from 0.1% to 5% of the total area of said film passage layer,
  said medium apertures have a total open area in the range from 1% to 35% of the total area of said film passage layer,
  said large apertures have a total open area in the range from 1% to 30% of the total area of said film passage layer,
  said extra-large apertures have a total open area in the range from 1% to 25% of the total area of said film passage layer,
  said liquid transport apertures have a largest inner diagonal length and a smallest inner diagonal length, the ratio of said largest to said smallest inner diagonal length is in the range from 1 to 6.

2. The absorbent article according to claim 1 wherein said small apertures have a total open area in the range from 0.5% to 3% of the total area of said film passage layer, said medium apertures have a total open area in the range from 10% to 25% of the total area of said film passage layer, said large apertures have a total open area in the range from 5% to 15% of the total area of said film passage layer, said extra-large apertures have a total open area in the range from 10% to 20% of the total area of said film passage layer.

3. The absorbent article according to claim 1 wherein at least some of said liquid transport apertures have inner walls which depend at least 0.3 mm from the surface of said film passage layer, said inner walls depend in a direction towards said absorbent structure of said article.

4. The absorbent article according to claim 1 wherein said film passage layer has liquid transport apertures of 5, 6, 7, 8, 9 or 10 different aperture open areas.

5. The absorbent article according to claim 1 wherein the total open area of all said liquid transport apertures in said film passage layer is in the range form 15% to 40% of the total area of said film passage layer.

6. The absorbent article according to claim 1 wherein the smallest edge to edge distance between large and/or extra-large apertures in said film passage layer is at least 0.5 mm.

7. The absorbent article according to claim 1 wherein said topsheet comprises more than one passage layer.

8. The absorbent article according to claim 1 wherein said liquid passage apertures are homogeneously distributed.

* * * * *